US 8,771,172 B2

(12) United States Patent
Bergen et al.

(10) Patent No.: US 8,771,172 B2
(45) Date of Patent: Jul. 8, 2014

(54) SENSOR SYSTEM AND METHOD FOR IMAGE CAPTURE OF AN OBJECT

(75) Inventors: Tobias Bergen, Erlangen (DE); Christian Münzenmayer, Nürnberg (DE); Christian Winter, Uttenreuth (DE); Thomas Wittenberg, Erlangen (DE)

(73) Assignees: Fraunhofer-Gesellschaft zur Förderung der angewandten Forschung e.V., München (DE); Friedrich-Alexander-Universität Erlangen-Nürnberg, Erlangen (DE)

( * ) Notice: Subject to any disclaimer, the term of this patent is extended or adjusted under 35 U.S.C. 154(b) by 244 days.

(21) Appl. No.: 13/148,216

(22) PCT Filed: Feb. 1, 2010

(86) PCT No.: PCT/EP2010/000574
§ 371 (c)(1),
(2), (4) Date: Aug. 5, 2011

(87) PCT Pub. No.: WO2010/089066
PCT Pub. Date: Aug. 12, 2010

(65) Prior Publication Data
US 2011/0288373 A1 Nov. 24, 2011

(30) Foreign Application Priority Data
Feb. 6, 2009 (DE) .......................... 10 2009 007 868

(51) Int. Cl.
*A61B 1/04* (2006.01)
*A61B 1/05* (2006.01)
*A61B 1/00* (2006.01)

(52) U.S. Cl.
CPC ... *A61B 1/04* (2013.01); *A61B 1/05* (2013.01); *A61B 1/00009* (2013.01); *A61B 1/00163* (2013.01); *A61B 1/00181* (2013.01); *A61B 1/00193* (2013.01)
USPC ............................ 600/109; 600/111; 600/117

(58) Field of Classification Search
CPC ........ A61B 1/04; A61B 1/05; A61B 1/00009; A61B 1/00163; A61B 1/00181; A61B 1/00193
USPC .................................. 600/109, 111, 113, 117
See application file for complete search history.

(56) References Cited

U.S. PATENT DOCUMENTS 5,471,988 A * 12/1995 Fujio et al. .................... 600/439
5,588,434 A * 12/1996 Fujimoto ...................... 600/443
(Continued)

FOREIGN PATENT DOCUMENTS

DE 100 18 673 A1 11/2000
DE 102 08 437 A1 9/2003
(Continued)

OTHER PUBLICATIONS

Irani et al., "All About Direct Methods", (http://citeseer.ist.psu.edu/viewdoc/summary?doi=10.1.1.37.2273).
(Continued)

Primary Examiner — John P Leubecker
Assistant Examiner — Arnaldo Torres Diaz
(74) Attorney, Agent, or Firm — McGlew and Tuttle, P.C.

(57) ABSTRACT

In a sensor system and a corresponding method for image capture of an object, an imaging sensor is arranged in a recording area of an optical sensor, the recording area being defined for the object, in such a way as to be essentially stationary relative to said object. By means of an evaluation unit, relative movements between the imaging sensor and the object can be derived from the recorded image data of the optical sensor, and a three-dimensional object image can be reconstructed from the imaging data as a function of the relative movements. When determining the relative movements, it is in particular possible as well to detect relative movements caused by the object's own motion which can be taken into account when reconstructing the object image. As a result, a high image quality of the object image is achieved.

14 Claims, 5 Drawing Sheets

(56) References Cited

U.S. PATENT DOCUMENTS

| | | | |
|---|---|---|---|
| 5,957,849 A * | 9/1999 | Munro | 600/459 |
| 6,554,771 B1 * | 4/2003 | Buil et al. | 600/459 |
| 7,912,321 B1 * | 3/2011 | Simonson | 382/294 |
| 2004/0167402 A1 * | 8/2004 | Jones et al. | 600/437 |
| 2005/0256402 A1 * | 11/2005 | Kawashima et al. | 600/437 |
| 2005/0283309 A1 * | 12/2005 | Sonoura | 701/207 |
| 2006/0116575 A1 * | 6/2006 | Willis | 600/434 |
| 2007/0167784 A1 * | 7/2007 | Shekhar et al. | 600/443 |
| 2007/0232922 A1 * | 10/2007 | Kohno | 600/459 |
| 2008/0027279 A1 * | 1/2008 | Abou El Kheir | 600/111 |
| 2008/0030578 A1 * | 2/2008 | Razzaque et al. | 348/143 |
| 2008/0119727 A1 * | 5/2008 | Barbagli et al. | 600/424 |
| 2008/0281189 A1 * | 11/2008 | Komuro et al. | 600/424 |
| 2008/0281236 A1 * | 11/2008 | Eshel et al. | 601/2 |
| 2009/0216122 A1 * | 8/2009 | Faragalla | 600/439 |
| 2010/0198045 A1 * | 8/2010 | Razzaque et al. | 600/407 |
| 2011/0122229 A1 * | 5/2011 | Cinquin et al. | 348/47 |
| 2011/0190629 A1 * | 8/2011 | Guenther et al. | 600/437 |

FOREIGN PATENT DOCUMENTS

| | | |
|---|---|---|
| EP | 0 961 135 B1 | 11/2002 |
| EP | 1 504 721 A1 | 2/2005 |
| WO | 2006/127142 A2 | 11/2006 |

OTHER PUBLICATIONS

Torr et al., "Feature Based Methods for Structure and Motion Estimation", (http://citeseerx.ist.psu.edu/viewdoc/summary?doi=10.1.1.37.1517).

* cited by examiner

SENSOR SYSTEM AND METHOD FOR IMAGE CAPTURE OF AN OBJECT

CROSS REFERENCE TO RELATED APPLICATIONS

This application is a United States National Phase application of International Application PCT/EP2010/000574 and claims the benefit of priority under 35 U.S.C. §119 of German Patent Application, Serial No. 10 2009 007 868.1, the entire contents of which are incorporated herein by reference.

FIELD OF THE INVENTION

The invention relates to a sensor system and to a method for image capture of an object.

BACKGROUND OF THE INVENTION

Imaging techniques for the capture of objects have become very important in the most various fields of application. Typical fields of application include the imaging of organs for medical applications as well as material and component testing for industrial purposes. For example, an ultrasonic sensor for medical purposes is able to produce three-dimensional tissue images, thus enabling one to identify the contours of a tumor so that a targeted therapeutic intervention can be planned and performed. In order to capture the three-dimensional structure of the object, it is necessary to produce a plurality of two-dimensional sectional images which are staggered relative to each other and are then combined to produce a three-dimensional object image. In this regard, the quality of the three-dimensional object image depends on the accuracy with which the individual two-dimensional sectional images are combined. In order to combine the individual sectional images, it is necessary to determine the movement of the ultrasonic sensor relative to the object as said movement represents the positions and orientations of the individual sectional images relative to one another.

EP 0 961 135 B1 discloses a sensor system for recording ultrasonic sectional images which is provided with an ultrasonic probe equipped with a position sensor that allows correct positioning of the recorded sectional images when the ultrasonic probe is moved during recording. Due to the fact that the position sensor provides absolute positional data in a defined reference coordinate system, the movement of the ultrasonic probe can be taken into account when reconstructing a three-dimensional object image from the sectional images. A drawback of this system is that an object's own motion is not detectable by the position sensor when recording the sectional images as a motion of this type has no influence on the position of the ultrasonic probe. Consequently, relative movements between the ultrasonic probe and the object which are due to the object's own motion are not detected and are not taken into account when reconstructing the three-dimensional object image, which results in a poor image quality.

SUMMARY OF THE INVENTION

It is therefore an object of the invention to produce a sensor system for image capture of an object which allows relative movements between an imaging sensor and the object caused by the object's own motion to be easily detected.

This object is achieved by a sensor system for image capture of an object, the sensor system comprising an imaging sensor for recording imaging data of an object to be captured, comprising an optical sensor for recording image data of the imaging sensor and of the object, with the imaging sensor being arranged in a recording area of the optical sensor which recording area has been defined for the object, and with the imaging sensor being arranged relative to the optical sensor in such a way as to be essentially stationary, and comprising an evaluation unit for evaluating the imaging data and the image data, with the evaluation unit being designed in such a way that a relative movement between the imaging sensor and the object is determinable from the image data, and a three-dimensional object image is reconstructible from the imaging data as a function of the determined relative movement.

The optical sensor allows one to record image data of the imaging sensor and of the object. The stationary arrangement of the imaging sensor relative to the optical sensor ensures that relative movements between these sensors are essentially prevented. The imaging sensor allows imaging data of the object to be recorded along with the image data, with the result that imaging data as well as image data are in each case provided at the same time. The evaluation unit allows the relative movement between the imaging sensor and the object to be obtained from the image data at successive points in time. In this process it is not only the relative movement caused by the imaging sensor's own motion that is taken into account but also relative movements caused by the object's own motion. By means of the relative movements obtained from the image data for particular points in time, the imaging data can be spatially allocated to one another in a very precise manner. This allows three-dimensional object images to be reconstructed at high accuracy even if the object moves, thus allowing a high image quality to be achieved.

The own motion of an object may be caused by a motion of the entire object such as the motion of organs due to respiration or blood circulation, or by a deformation of the object such as the deformation of an organ which is due to external influences. External influences may in particular also refer to influences of the sensor system which comes into contact with the object while the imaging data are being recorded. Such deformations can be recognized from the image data, thus allowing the associated imaging data either to be discarded when reconstructing the three-dimensional object image as they are usually of no use; if the image data have been recorded in real time, it is possible to dispense with recording associated imaging data altogether until a suitable recording position of the imaging sensor has been found in which the object is not deformed.

The imaging sensor can be designed to record two-dimensional sectional images or three-dimensional volume segment images which can be combined to produce a three-dimensional object image using the determined relative movements. The imaging sensor may for example be an ultrasonic sensor.

The relative movements can be determined from the image data on the basis of pixels which means that the pixels are examined to find out how they move in space in relation to temporally adjacent image data. Alternatively, the relative movements can also be determined on the basis of features which means that stable structures are identified in surface images allocated to the image data which are then examined to find out how they move in space.

The rigid mechanical connection of a sensor system, in which the imaging sensor is securely connected to the optical sensor by a rigid connection element, ensures a stationary arrangement of the sensors relative to each other. This is particularly true if forces are applied to the sensor system.

A sensor system, in which the connection element is at least partially arranged in the recording area, ensures high mechanical rigidity as the connection element is arranged close to the sensors.

A sensor system, in which the imaging sensor is an ultrasonic sensor, is suitable for capturing organs in medical applications.

A sensor system, in which the imaging sensor is designed in such a way that imaging data for two-dimensional sectional images of the object are recordable, allows two-dimensional sectional images to be recorded which can be combined by means of the evaluation unit to produce a three-dimensional object image.

A sensor system, in which the imaging sensor is designed in such a way that imaging data for three-dimensional volume segment images of the object are recordable, allows three-dimensional volume segment images to be recorded which can be combined to produce a three-dimensional object image that shows a larger total volume of the object.

A sensor system, in which a position measuring device is provided for determining absolute positional data of the imaging sensor, allows absolute positional data of the imaging sensor to be detected so that the imaging sensor can be related to an absolute coordinate system. The position measuring device allows relative movements caused by the imaging sensor's own motion to be distinguished from relative movements caused by the object's own motion.

A sensor system, in which the position measuring device is electromagnetic, is freely movable in space. In contrast to optical position measuring devices, an optical line of sight is not required for position measurement.

A sensor system, in which the position measuring device comprises an electromagnetic probe which is arranged in the region of the rigidly connected sensors, allows absolute positional data of the imaging sensor to be determined at high accuracy. The electromagnetic probe can for example be arranged on the imaging sensor directly. Alternatively, the electromagnetic probe can be arranged on the connection element or the optical sensor as they are rigid and connected to the imaging sensor at known distances.

A sensor system, in which the evaluation unit is designed in such a way that the relative movement between the imaging sensor and the object is determinable taking into account the absolute positional data, allows the relative movement to be determined at high accuracy as the detected absolute positional data are combined with the relative movement. For example, the relative movement can be detected more precisely by performing a rough position measurement of the imaging sensor by means of the absolute positional data which measurement is then combined with the determined relative movement. Errors occurring when determining the relative movement, which may for example occur in pixel- or feature-based methods when large movements are performed, may be detected and corrected by comparing them to the absolute positional data. When using imaging sensors which are usually in direct contact with the object or are moved across the object at a distance thereto, it is necessary for determining the relative movements to detect in particular both translation and rotation in a plane which is tangential to the surface of the object as well as a tilting movement relative to the object. In this regard, it is advantageous to compare the detected relative movement with the absolute positional data.

An endoscopic system comprising a stem which comprises a first end which faces away from an object to be captured, and a second end which faces the object, and comprising a sensor system for image capture of an object according to the invention, with the imaging sensor and the image sensor being arranged at the second end, allows regions of the object to be captured which are difficult to access. In the endoscopic system, the optical sensor which is relevant for detecting the relative movements is arranged directly at the point where the actual movement occurs, in other words the second end, which allows the relative movements to be determined at high accuracy.

An endoscopic system, in which the stem is flexible at least in the region of the second end, ensures improved accessibility of object regions which are difficult to access. The arrangement of the optical sensor at the second end prevents inaccuracies during relative movement detection which are due to a deformation of the flexible stem and/or vibrations.

It is another object of the invention to provide a method for image capture of an object which allows relative movements between an imaging sensor and the object caused by an object's own motion to be easily detected.

This object is achieved by a method for image capture of an object, the method comprising the steps of providing a sensor system comprising an imaging sensor for recording imaging data of an object to be captured, and an optical sensor for recording image data of the imaging sensor and of the object, with the imaging sensor being arranged in a recording area of the optical sensor which recording area has been defined for the object, and with the imaging sensor being arranged relative to the optical sensor in such a way as to be essentially stationary, recording imaging data of the object by means of the imaging sensor and recording image data of the imaging sensor and of the object by means of the optical sensor at identical points in time, and evaluating the imaging data and the image data in such a way that a relative movement between the imaging sensor and the object is determined from the image data, and a three-dimensional object image is reconstructed from the imaging data as a function of the determined relative movement.

The advantages of the method according to the invention correspond to the advantages of the sensor system according to the invention which have already been described.

Further features, advantages and details of the invention will become apparent from the ensuing description of an embodiment by means of the drawing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
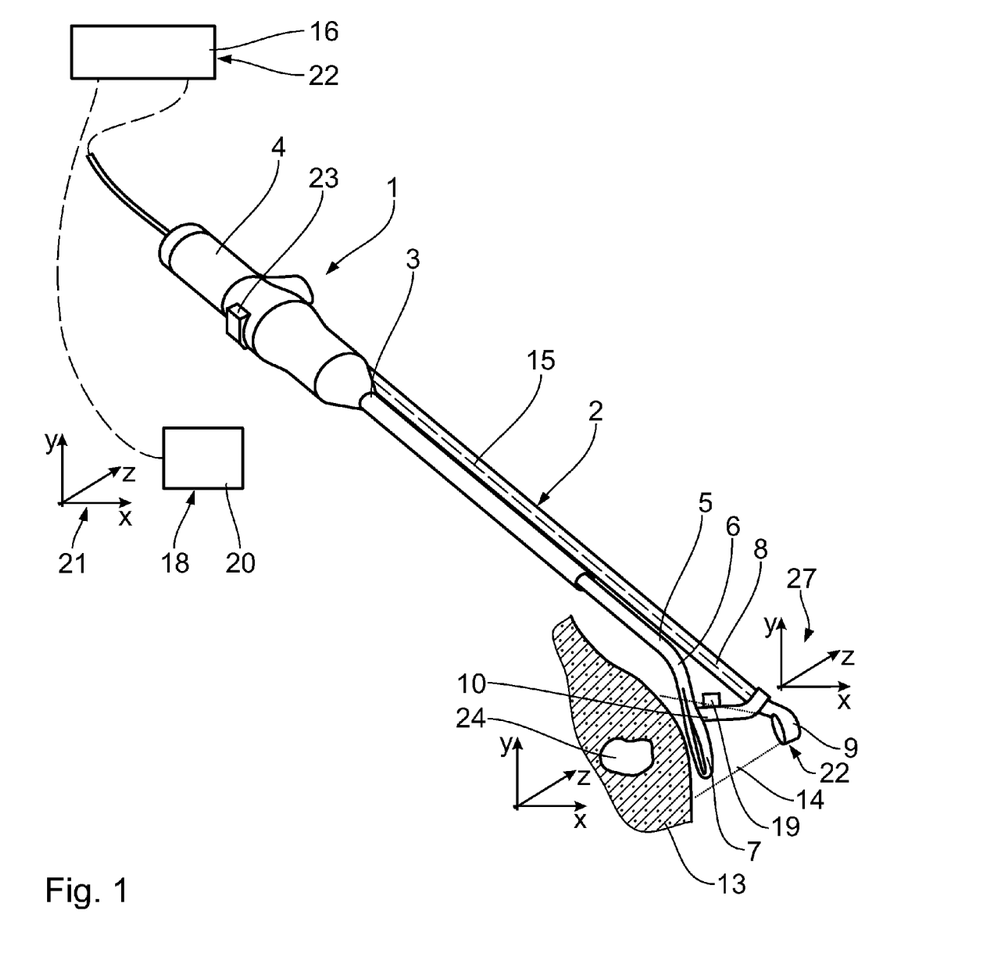
FIG. 1 is a perspective view of an endoscopic system with a sensor system comprising an imaging sensor and an optical sensor.

An endoscopic system 1 comprises a stem 2 with a first end 3 at which a handle 4 is arranged. A second end 5 of the stem 2 is in the shape of a V. An imaging first sensor 7 is arranged at a first stem portion 6. Correspondingly, an optical second sensor 9 is arranged at a second stem portion 8. Near the sensors 7, 9, a rigid mechanical connection element 10 extends between the stem portions 6, 8 for rigidly connecting the sensors 7, 9 with each other. The sensors 7, 9 are thus arranged essentially stationarily with respect to each other. The stem portions 6, 8 are flexible so that the stationarily connected sensors 7, 9 are movably arranged at the second end 5 of the stem 2.

The imaging sensor 7 is an ultrasonic sensor and forms part of an ultrasonic probe which is not shown in more detail. The imaging sensor 7 is designed for recording imaging data for two-dimensional sectional images 11 and/or three-dimensional volume segment images 12 of an object 13 to be captured.

The optical sensor 9 is a miniature video sensor, for example a tip-chip videoscope. The optical sensor 9 has a recording area 14 facing the imaging sensor 7 in which the imaging sensor 7 and part of the connection element 10 are arranged. As the imaging sensor 7 is located in the recording area 14, it is possible to record image data of the imaging sensor 7 and even of the object 13 when the imaging sensor 7 is positioned accordingly. The optical sensor 9 thus forms a camera for observing the imaging sensor 7 and the object 13.

The sensors 7, 9 are connected to an evaluation unit 16 via signal lines 15 which are guided in the stem 2. Similarly, the sensors 7, 9 are connected to an energy supply unit via supply lines which are not shown in more detail.

The evaluation unit 16 serves to evaluate the recorded imaging data and the recorded image data. The evaluation unit 16 is designed in such a way that relative movements between the imaging sensor 7 and the object 13 are derivable from the image data so that a three-dimensional object image 17 of the object 13 is reconstructible from the imaging data as a function of the determined relative movements.

A position measuring device 18 is provided for detecting absolute positional data of the imaging sensor 7. The position measuring device 18 is electromagnetic and comprises an electromagnetic probe 19 in the form of a coil as well as a probe detection unit 20. The probe 19 is arranged in the region of the rigidly connected sensors 7, 9. FIG. 1 shows an exemplary arrangement of the probe 19 at the connection element 10. The probe detection unit 20 serves to generate a magnetic field in which the absolute position of the probe 19 is detectable in a first Cartesian coordinate system 21. The probe detection unit 20 is connected to the evaluation unit 16 via signal lines 22 so that the relative movements between the imaging sensor 7 and the object 13 are detectable by means of the evaluation unit 16 taking into account the absolute positional data of the imaging sensor 7.

The imaging sensor 7, the optical sensor 9, the connection element 10, the evaluation unit 16 and the position measuring device 18 together form a sensor system 22. The sensor system 22 is part of the endoscopic system 1. The endoscopic system 1 has several operating elements 23 in the region of the handle 4 for operating the sensors 7, 9.

The following is a description of the functioning of the endoscopic system 1 and of the sensor system 22. By means of the endoscopic system 1, the sensors 7, 9 are brought into close proximity to the object 13. The object 13 may for example be an organ to be captured which moves by itself. An object's own motion may for example be the result of a motion of the entire organ due to respiration or of forces applied to parts of the organ.

Figure 2:
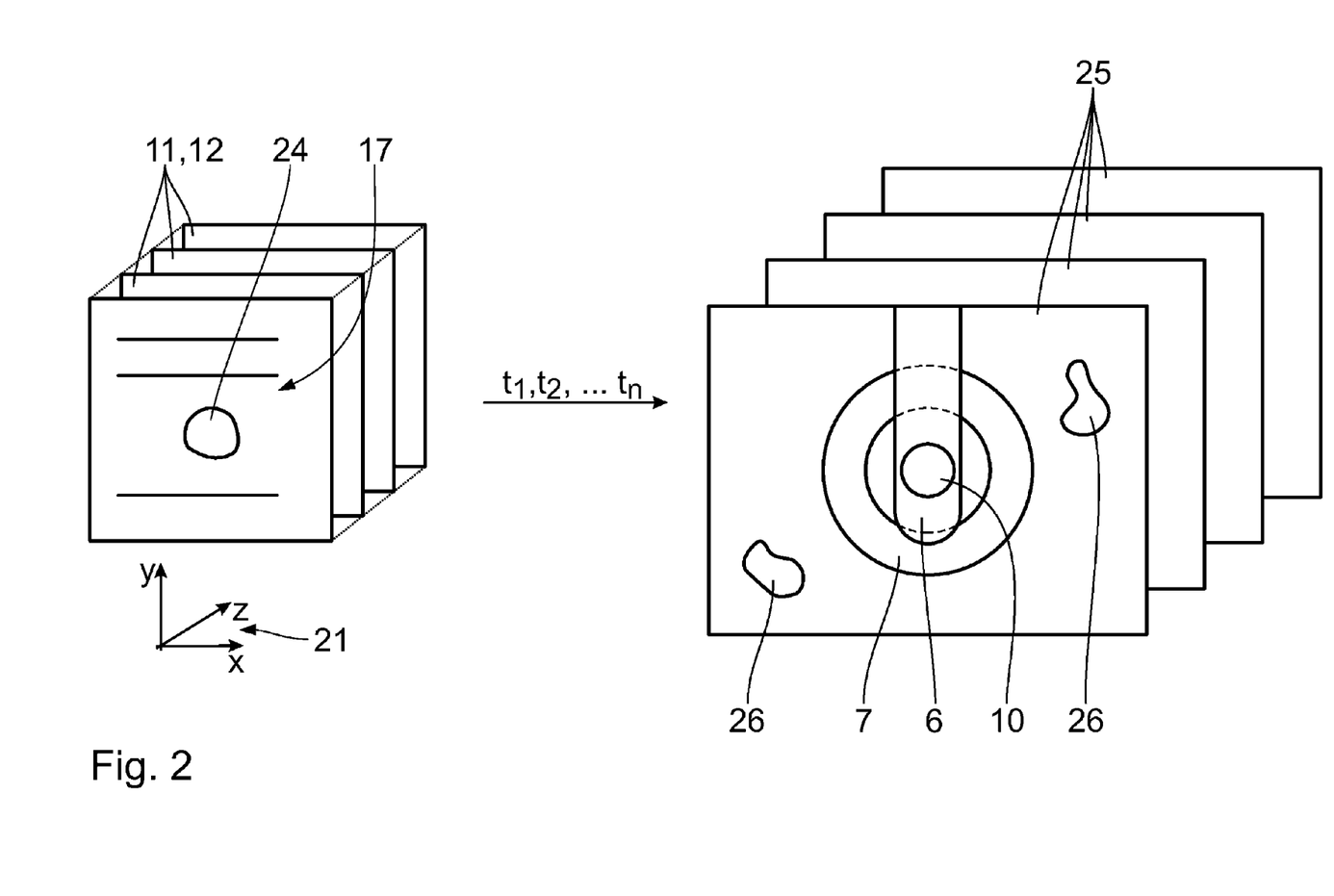
FIG. 2 is a schematic illustration of sectional images recorded by means of the imaging sensor and surface images recorded by means of the optical sensor.

FIG. 1 shows the sensors 7, 9 in a recording position. In this recording position, a sequence of imaging data and a corresponding sequence of image data are recorded by means of the imaging sensor 7 and the optical sensor 9. During recording, the imaging sensor 7 is moved in space through the first coordinate system 21 in such a way that first imaging data are recorded in a first recording position, second imaging data are recorded in a second recording position and associated $n^{th}$ imaging data are recorded in an $n^{th}$ recording position which are then transmitted to the evaluation unit 16. The imaging data contain information for a corresponding first to $n^{th}$ sectional image 11. In other words, the imaging sensor 7 is used to record a sequence of sectional images 11 in various recording positions. The individual sectional images 11 are recorded at different points in time t, with the first sectional image 11 being recorded at a first point in time $t_1$, the second sectional image 11 at a second point in time $t_2$ and the $n^{th}$ sectional image 11 at an $n^{th}$ point in time $t_n$. FIG. 2 shows an exemplary sequence of sectional images 11 which were recorded during a displacement in a z-direction. In the sectional images 11, a structure 24 is visible which lies below the object surface.

In the evaluation unit 16, the sectional images 11 are combined to produce the three-dimensional object image 17. In order to do so, the evaluation unit 16 requires information about the position of the sectional images 11 relative to one another. In order to obtain this information, first image data to $n^{th}$ image data are recorded by means of the optical sensor 9 at the points in time $t_1$ to $t_n$. The image data are transmitted to the evaluation unit 16 where they are converted into corresponding surface images 25 of the object surface. As shown by FIG. 2, the surface images 25 show the imaging sensor 7 comprising the stem 2 as well as surface structures 26. As the imaging sensor 7 and the stem 2 are arranged stationarily in a second coordinate system 27 of the optical sensor 9, relative movements between the imaging sensor 7 and the object 13 are characterized by movements of the surface structures 26 in the sequence of surface images 25.

Figure 3:
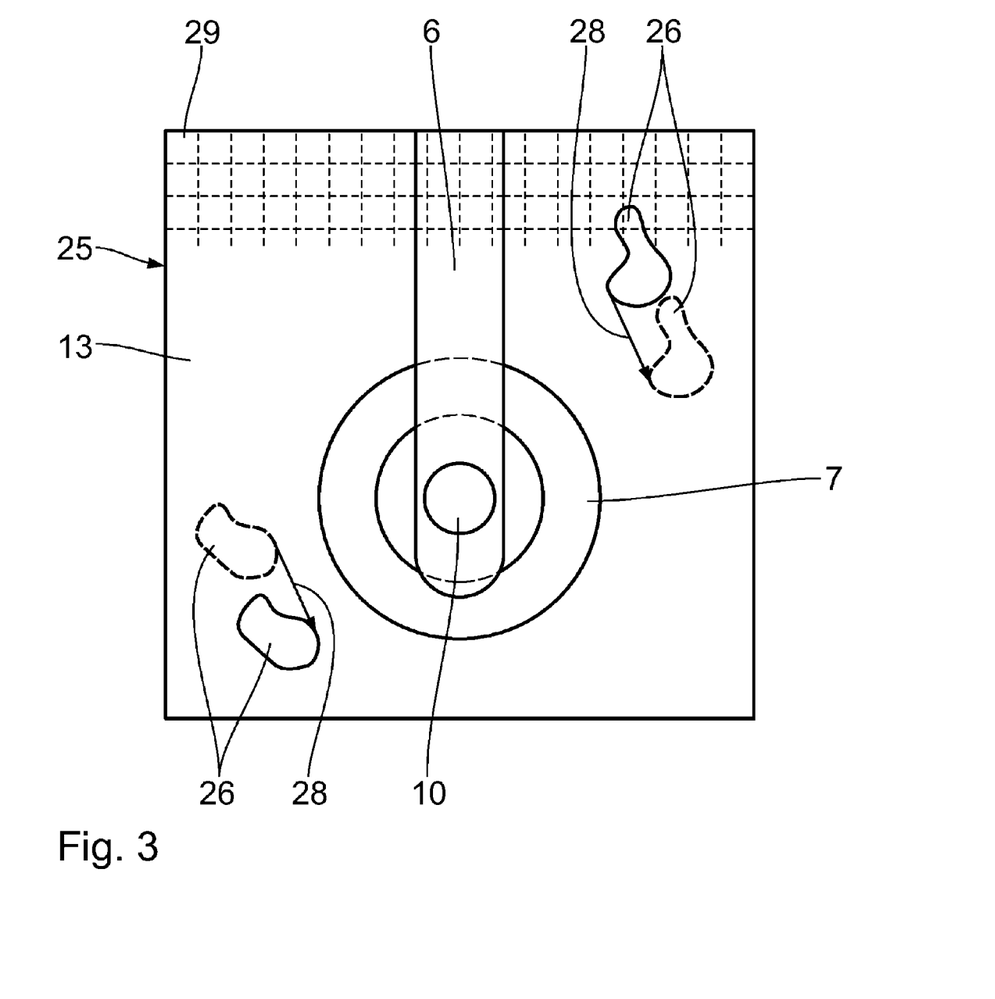
FIG. 3 is a schematic illustration of temporally successive and congruent surface images for detecting relative movements between the imaging sensor and the object.

In order to spatially allocate the sectional images 11 to one another, relative movements between the imaging sensor 7 and the object 13 are derived from the surface images 25. FIG. 3 shows two surface images 25 at successive points in time t which are placed on top of each other in such a way as to be congruent. The surface structures 26 at a first point in time, for example at $t_1$, are represented by a continuous line in FIG. 3. The surface structures 26 at a subsequent second point in time, for example at $t_2$, are represented by a dashed line in FIG. 3. Due to movements of the imaging sensor 7 and/or the object 13, the surface structures 26 have different positions in the second coordinate system 27, in other words in the surface images 25. By means of the evaluation unit 16, a respective relative movement between two successive points in time is derived from the different positions of the surface structures 26.

To this end, one or several displacement vectors 28 are determined using a pixel-based or a feature-based method. The displacement vectors 28 characterize the relative movement between the imaging sensor 7 and the object 13. These displacement vectors 28 provide the basis for spatially allocating the respective sectional images 11 to one another.

In the pixel-based method, the displacement vectors 28 are obtained from individual pixels 29 which are indicated in FIG. 3. Further details concerning pixel-based methods can be found in the scientific article "All About Direct Methods"

by M. Irani and P. Anandan (http://citeseerx.ist.psu.edu/viewdoc/summary?doi=10.1.1.37.2273).

In the feature-based method, stable structures such as the surface structures 26 are selected from suitable image regions and identified in temporally adjacent surface images 25. The stable structures form the basis for determining the displacement vectors 28. Further details concerning feature-based methods can be found in the scientific article "Feature Based Methods for Structure and Motion Estimation" by P. H. S. Torr and A. Zisserman (http://citeseerx.ist.psu.edu/viewdoc/summary?doi=10.1.1.37.1517).

Compared to pixel-based methods, feature-based methods calculate the displacement vectors 28 at a relatively high speed. In contrast to that, pixel-based methods allow displacement vectors 28 to be determined with sufficient precision even if a feature-based method is not able to provide any stable structures. Pixel-based methods are for example able to determine respective displacement vectors 28 in the region of a color gradient.

While the imaging data are being recorded, absolute positional data of the imaging sensors 7 are determined at the first time $t_1$ up to the $n^{th}$ time $t_n$ by means of the position measuring device 18. The position measuring device 18 is a conventional electromagnetic tracking system which generates a magnetic field in which the probe 19, which is in the form of a coil, can be moved as well as detected and located by means of the detection unit 20. The absolute positional data thus contain information about the position and orientation of the probe 19 in the first coordinate system 21. As the probe 19 has a constant defined distance from the imaging sensor 7, it is possible to derive, by means of the evaluation unit 16, the absolute positional data of the imaging sensor 7 from the absolute positional data of the probe 19.

The absolute positional data of the imaging sensor 7 may be utilized for comparison and/or completion in the evaluation unit 16 when determining the relative movements. Pixel- or feature-based for example show problems when determining large relative movements. Consequently, it is advantageous when large relative movements occur to obtain a reference value for the relative movement by means of the absolute positional data, which reference value is the starting point for the pixel-based or feature-based method. The absolute positional data thus provide a rough value for the relative movement which rough value is then defined more precisely using the pixel- or feature-based method. Combining the absolute positional data with the results of the pixel- or feature-based method thus allows the relative movements to be determined in an extremely precise manner. The electromagnetic position measuring device 18 does not affect the mobility of the endoscope 1 when capturing the object 13.

Figure 4:
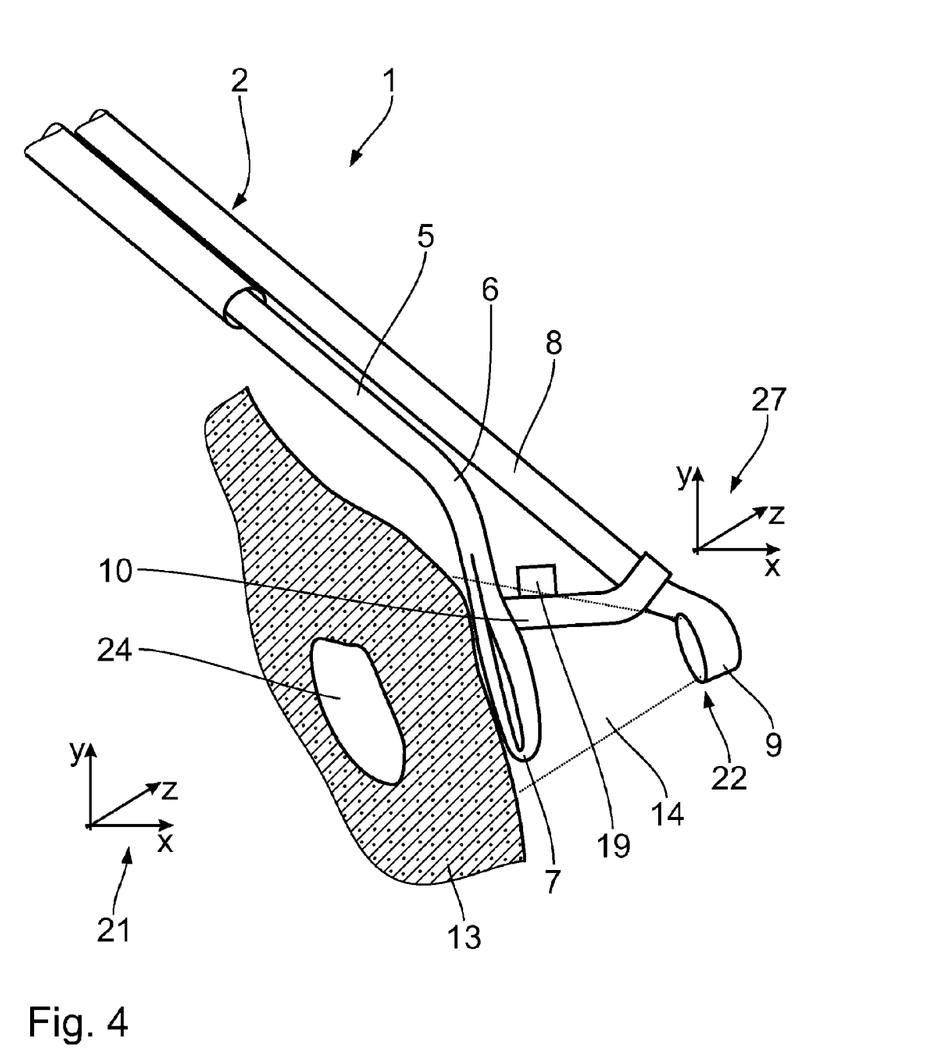
FIG. 4 is a perspective view of the endoscopic system in FIG. 1 in a position which deforms the object.
Figure 5:
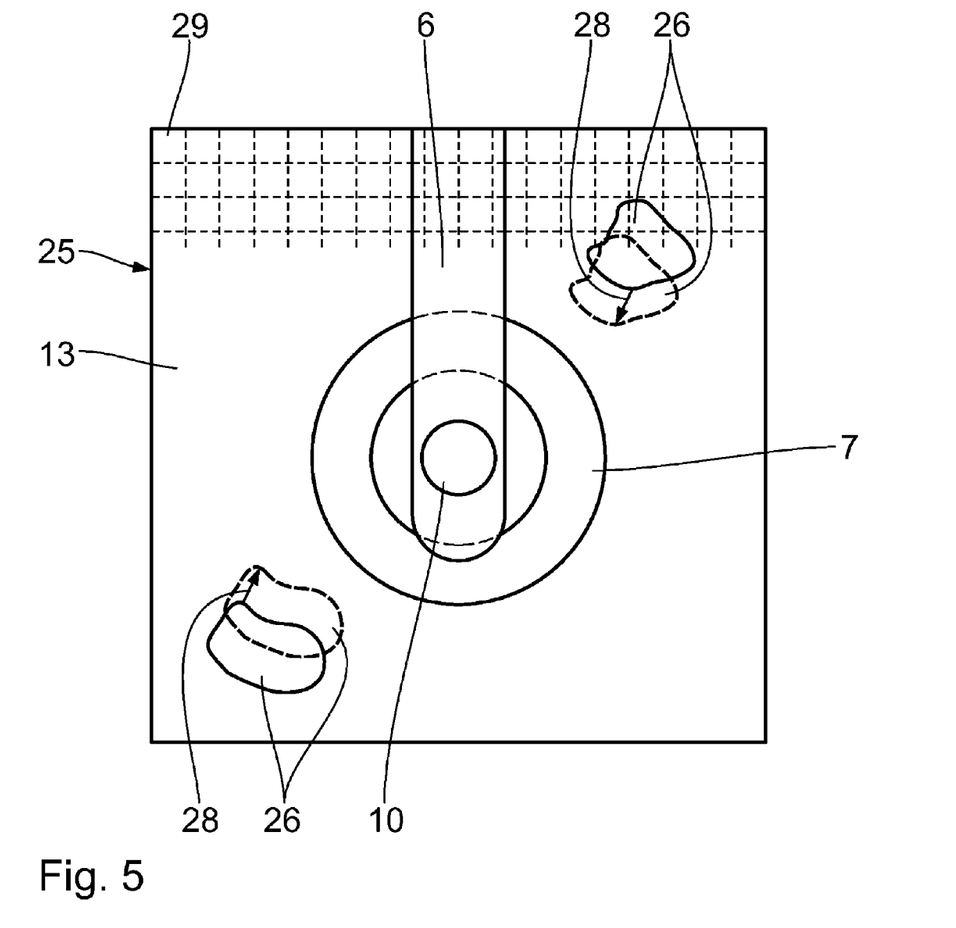
FIG. 5 is a schematic illustration of two temporally successive surface images according to FIG. 3 when the object is being deformed.

When determining the relative movements, it is possible as well to detect and determine relative movements caused by the object's 13 own motion, thus allowing the sectional images 11 to be precisely allocated to one another in space and to be combined to produce the three-dimensional object image 17. Moreover, it is possible to detect, in the surface images 25, deformations of the object 13 which are caused by the application of a force. FIG. 4 for example shows a deformation of the object 13, for example an organ, which is caused by the imaging sensor 7 placed on top thereof. This also leads to a deformation of the structure 24 underneath the object surface, with the result that sectional images 11 recorded in this state cannot be combined with sectional images 11 recorded in a non-deformed state of the object 13 in such a way that a useful image is obtained. Consequently, sectional images 11 recorded in the deformed state either need to be sorted out by means of the evaluation unit 16 or they are not recorded at all. Deformations can easily be recognized in the surface images 25 as the deformation causes the surface structures 26 to move toward the imaging sensor 7. When determining the displacement vectors 28, deformations can be recognized by means of the displacement vectors 28 which point toward the imaging sensor 7. If the relative movements are constantly determined in the evaluation unit 16 in real time, the direction of the displacement vectors 28 allows a deformation to be recognized so that no corresponding sectional image 11 is recorded. Otherwise, the sectional image 11 recorded in the deformed state can easily be recognized and sorted out.

The above description applies accordingly if the imaging data characterize volume segment images 12 instead of sectional images 11 which are combined to produce the larger object image 17.

The invention provides an imaging sensor system and a corresponding imaging method which allows relative movements between the imaging sensor 7 and the object 13 caused by the object's 13 own motion to be detected. By means of these relative movements, recorded sectional images 11 or volume segment images 12 can be spatially allocated to one another and combined to produce a three-dimensional object image 17. As the object's 13 own motion is taken into account as well, the images can be allocated to one another in a very precise manner so that a correspondingly high image quality of the object image is achieved. This method in particular allows dynamic organ structures to be captured in such a way that high-quality three-dimensional images are obtained.

The surface images 25, which have been recorded at successive points in time t, are used to determine respective displacement vectors or a displacement vector field, respectively, which describes the spatial allocation of the respective sectional images 11 or volume segment images 12. The surface images 25 are recorded by means of the optical sensor 9 which is a miniature video sensor; consequently, the endoscopic system 1 also serves as a videoscope at the same time.

Due to the rigid connection of the sensors 7, 9, the system is independent of external tracing methods such as mechanical or optical tracking. As changes in the object, such as deformations, are locally taken into account, conventional tracking methods can be complemented and/or corrected as well. The invention has a high tolerance with respect to the object's own motion such as an organ motion due to blood circulation or respiration.

The invention is applicable both in the field of medicine and for industrial purposes. As already described above, the system can be used to capture organ motion for medical applications while in industry, the system allows one to take into account movements and/or deformations of components to be examined. In medicine, the endoscopic system 1 or the sensor system 22, respectively, can be used extracorporeally as well as intracorporeally. An ultrasonic probe may for example be used in the B-mode to record intracorporeal abdominal images of the liver. Examples of technical applications in industry include material testing, testing of technical fabrics, foams and insulation materials as well as of components for aerospace engineering and rotor blades for wind energy plants. Testing may in particular be performed during operation (structural health monitoring) and in regions which are difficult to access such as technical cavities.

While specific embodiments of the invention have been shown and described in detail to illustrate the application of the principles of the invention, it will be understood that the invention may be embodied otherwise without departing from such principles.

The invention claimed is:

1. A sensor system for image capture of an object, the sensor system comprising:
   an imaging sensor for recording imaging data of an object to be captured;
   an optical sensor for recording image data of the imaging sensor and of the object, said imaging sensor being arranged in a recording area of the optical sensor which said recording area has been defined for the object, the imaging sensor being arranged relative to the optical sensor in such a way as to be essentially stationary; and
   an evaluation unit for evaluating the imaging data and the image data, with the evaluation unit being designed in such a way that a relative movement between the imaging sensor and the object is determinable from the image data and a three-dimensional object image is reconstructible from the imaging data as a function of the determined relative movement and said evaluation unit being designed such that a deformation of the object due to an influence of the imaging sensor is recognizable by means of said image data, wherein said deformation is recognizable by means of several displacement vectors which point toward the imaging sensor, said displacement vectors characterizing the relative movement between the imaging sensor and the object, the evaluation unit being designed such that at least one of no imaging data are recordable and recorded imaging data are discardable in case said deformation is recognized.

2. A sensor system according to claim 1, wherein the imaging sensor is securely connected to the optical sensor by a rigid connection element.

3. A sensor system according to claim 2, wherein the connection element is at least partially arranged in the recording area.

4. A sensor system according to claim 1, wherein the imaging sensor is an ultrasonic sensor.

5. A sensor system according to claim 1, wherein the imaging sensor is designed in such a way that imaging data for two-dimensional sectional images of the object are recordable.

6. A sensor system according to claim 1, wherein the imaging sensor is designed in such a way that imaging data for three-dimensional volume segment images of the object are recordable.

7. A sensor system according to claim 1, wherein a position measuring device is provided for determining absolute positional data of the imaging sensor.

8. A sensor system according to claim 7, wherein the position measuring device is electromagnetic.

9. A sensor system according to claim 8, wherein the position measuring device comprises an electromagnetic probe which is arranged in the region of the rigidly connected sensors.

10. A sensor system according to claim 7, wherein the evaluation unit is designed in such a way that the relative movement between the imaging sensor and the object is determinable taking into account the absolute positional data.

11. An endoscopic system comprising:
    a stem comprising a first end which faces away from an object to be captured and a second end which faces the object; and
    a sensor system for image capture of the object, said sensor system comprising:
        an imaging sensor for recording imaging data of an object to be captured;
        an optical sensor for recording image data of the imaging sensor and of the object, said imaging sensor being arranged in a recording area of the optical sensor, said recording area being defined for the object, said imaging sensor being arranged relative to the optical sensor in such a way as to be essentially stationary; and
        an evaluation unit for evaluating the imaging data and the image data, said evaluation unit determining a relative movement between the imaging sensor and the object from the image data and a three-dimensional object image is reconstructed from the imaging data as a function of the determined relative movement, said evaluation unit determining a deformation of the object due to said imaging sensor based on said image data, said imaging sensor and the image sensor being arranged at the second end, wherein said deformation is recognizable by means of several displacement vectors which point toward the imaging sensor, said displacement vectors characterizing the relative movement between the imaging sensor and the object, at least one of no imaging data being recorded and recorded imaging data being discarded in case said deformation is recognized.

12. An endoscopic system according to claim 11, wherein the stem is flexible at least in the region of the second end.

13. A method for image capture of an object, the method comprising the following steps:
    providing a sensor system comprising an imaging sensor for recording imaging data of an object to be captured, and an optical sensor for recording image data of the imaging sensor and of the object, said imaging sensor being arranged in a recording area of the optical sensor which said recording area has been defined for the object, said imaging sensor being arranged relative to the optical sensor in such a way as to be essentially stationary;
    recording imaging data of the object by means of the imaging sensor and recording image data of the imaging sensor and of the object by means of the optical sensor at identical points in time; and
    evaluating the imaging data and the image data in such a way that a relative movement between the imaging sensor and the object is determined from the image data and a three-dimensional object image is reconstructed from the imaging data as a function of the determined relative movement and a deformation of the object due to an influence of said imaging sensor is determined via said image data, wherein said deformation is recognized by means of several displacement vectors, which point toward the imaging sensor, said displacement vectors characterizing the relative movement between the imaging sensor and the object, at least one of no imaging data being recorded and recorded imaging data being discarded in case said deformation is recognized.

14. A method according to claim 13, further comprising:
    providing a stem having a first stem portion and a second stem portion, said imaging sensor being connected to an end of said first stem portion and said optical sensor being connected to an end of said second stem portion, wherein said imaging sensor is located at a spaced location from said optical sensor, said imaging sensor being located opposite said optical sensor.

* * * * *

UNITED STATES PATENT AND TRADEMARK OFFICE
CERTIFICATE OF CORRECTION

PATENT NO.         : 8,771,172 B2
APPLICATION NO.    : 13/148216
DATED              : July 8, 2014
INVENTOR(S)        : Tobias Bergen et al.

Page 1 of 1

It is certified that error appears in the above-identified patent and that said Letters Patent is hereby corrected as shown below:

Title page, item [75]:
Inventor Christian Winter's address is Hildesheim

Signed and Sealed this
Thirtieth Day of September, 2014

Michelle K. Lee
*Deputy Director of the United States Patent and Trademark Office*